(12) United States Patent
Typpo

(10) Patent No.: US 7,423,758 B1
(45) Date of Patent: Sep. 9, 2008

(54) GLOSS SENSOR FOR A PAPER MACHINE

(75) Inventor: Pekka Typpo, Cupertino, CA (US)

(73) Assignee: Voith Patent GmbH, Heidenheim (DE)

( * ) Notice: Subject to any disclaimer, the term of this patent is extended or adjusted under 35 U.S.C. 154(b) by 0 days.

(21) Appl. No.: 11/829,431

(22) Filed: Jul. 27, 2007

(51) Int. Cl.
*G01N 21/55* (2006.01)

(52) U.S. Cl. .................................. 356/445; 356/448

(58) Field of Classification Search .............. 356/445, 356/448
See application file for complete search history.

(56) References Cited

U.S. PATENT DOCUMENTS

| | | | |
|---|---|---|---|
| 4,945,253 A | 7/1990 | Frohardt | 356/446 |
| 5,392,125 A * | 2/1995 | Reisser | 356/445 |
| 6,404,502 B2 | 6/2002 | Preston et al. | 356/445 |
| 6,507,403 B1 | 1/2003 | Belotserkovsky | 356/445 |
| 2006/0192957 A1* | 8/2006 | Frick et al. | 356/328 |

FOREIGN PATENT DOCUMENTS

| | | |
|---|---|---|
| EP | 0940501 | 8/1999 |
| WO | WO9849541 | 5/1998 |

* cited by examiner

*Primary Examiner*—Roy M Punnoose
(74) *Attorney, Agent, or Firm*—Taylor & Aust, P.C.

(57) ABSTRACT

A gloss sensor for optically measuring the gloss of a moving surface includes a housing having an exterior surface which is generally parallel with the moving surface. A light source is carried by the housing and configured for emitting a source beam of light. At least one light detector is carried by the housing. An optical prism is mounted to the housing at the exterior surface. The prism is configured to split the source beam into a reference beam which is reflected by the prism internally within the housing to the one or more light detectors, and a measurement beam which passes through the prism and is reflected by the moving surface to the one or more light detectors.

29 Claims, 2 Drawing Sheets

GLOSS SENSOR FOR A PAPER MACHINE

BACKGROUND OF THE INVENTION

1. Field of the Invention

The present invention relates to gloss sensors for optically measuring the gloss of a moving surface, and, more particularly, to a gloss sensor used to measure the gloss of a moving fiber web in a paper machine.

2. Description of the Related Art

In the paper making industry where paper is being produced at a high rate from a paper making machine, for quality and feedback control the paper is scanned crosswise by a moving a head containing a number of sensors to determine parameters such as basis weight, moisture and gloss. The final value of gloss is a rather arbitrary number determined by standards in the paper making industry; namely, TAPPI standard T 480 om-90 which involves projecting onto the paper surface an incident beam of light at a particular angle, detecting the reflected beam and measuring its intensity. To calibrate the above TAPPI standard a polished black glass standard is used. Then an intermediate standard which is calibrated against that may be a polished ceramic tile. Some gloss sensors actually mechanically carry such a tile in a moving measuring head and lower the tile into the light beam to calibrate the instrument. This, of course, is mechanically complicated and there are some problems of environmental conditions such as heat, dirt and also accurate positioning.

Another gloss measuring technique uses a separate reference beam apart from the incident measuring beam. Here there are two separate light sources and light detectors. Moreover, the light source is a different type than the standard source defined by the above TAPPI standards. Thus, the correlation to the industry standard is suspect.

It is also known to use a gloss sensor which is calibrated using an oscillation angle light source which with the same lamp has a "reference" to a light detector. A reference beam is split from the main beam emitted from the light source and passes through a recess in the housing which is external to the gloss sensor. The reference beam then passes across the recess and through a detector window to re-enter the gloss sensor, then through a lens, and finally changes angles at a reflector to impinge upon the light detector. An example of such a gloss sensor is disclosed in PCT/US98/08805, which is assigned to the assignee of the present invention. This type of gloss sensor works well, but is still somewhat bulky in size due to the geometric layout of the various components. Moreover, the recess in the gloss sensor housing may allow accumulation of dirt or debris which can affect the accuracy of the gloss sensor.

What is needed in the art is a gloss sensor which is compact and has a high accuracy and reliability.

SUMMARY OF THE INVENTION

The present invention provides a gloss sensor with a prism which is mounted flush with the exterior surface of the gloss sensor housing to avoid dirt and debris build-up affecting the source beam of light, and a reference beam which is generated internally by the prism and does not pass to the outside of the gloss sensor.

The invention in one form is directed to a gloss sensor for optically measuring the gloss of a moving surface. The gloss sensor includes a housing having an exterior surface which is generally parallel with the moving surface. A light source is carried by the housing and configured for emitting a source beam of light. At least one light detector is carried by the housing. An optical prism is mounted to the housing at the exterior surface. The prism is configured to split the source beam into a reference beam which is reflected by the prism internally within the housing to the one or more light detectors, and a measurement beam which passes through the prism and is reflected by the moving surface to the one or more light detectors.

The invention in another form is directed to a method of measuring the gloss of a moving surface. A gloss sensor housing is positioned such that an exterior surface of the housing is adjacent and generally parallel to the moving surface at a distance of between approximately 0.05 to 0.5 mm from the moving surface. A source beam of light is emitted from a light source carried by the housing, and the source beam is split into a reference beam and a measurement beam using an optical prism mounted to the housing at the exterior surface. The reference beam is reflected by the prism internally within the housing to the at least one light detector. The measurement beam passes through the prism and is reflected by the moving surface to the one or more light detectors. The reference beam and the measurement beam are received at the one or more light detectors carried by the housing.

An advantage of the present invention is that the gloss sensor is compact and can be miniaturized.

Another advantage is that the reference beam can be generated by the same prism which reflects the measurement beam from the moving surface.

Yet another advantage is that a secondary reference beam can be used.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention, in one form, and such exemplification is not to be construed as limiting the scope of the invention in any manner.

DETAILED DESCRIPTION OF THE INVENTION

Figure 1:
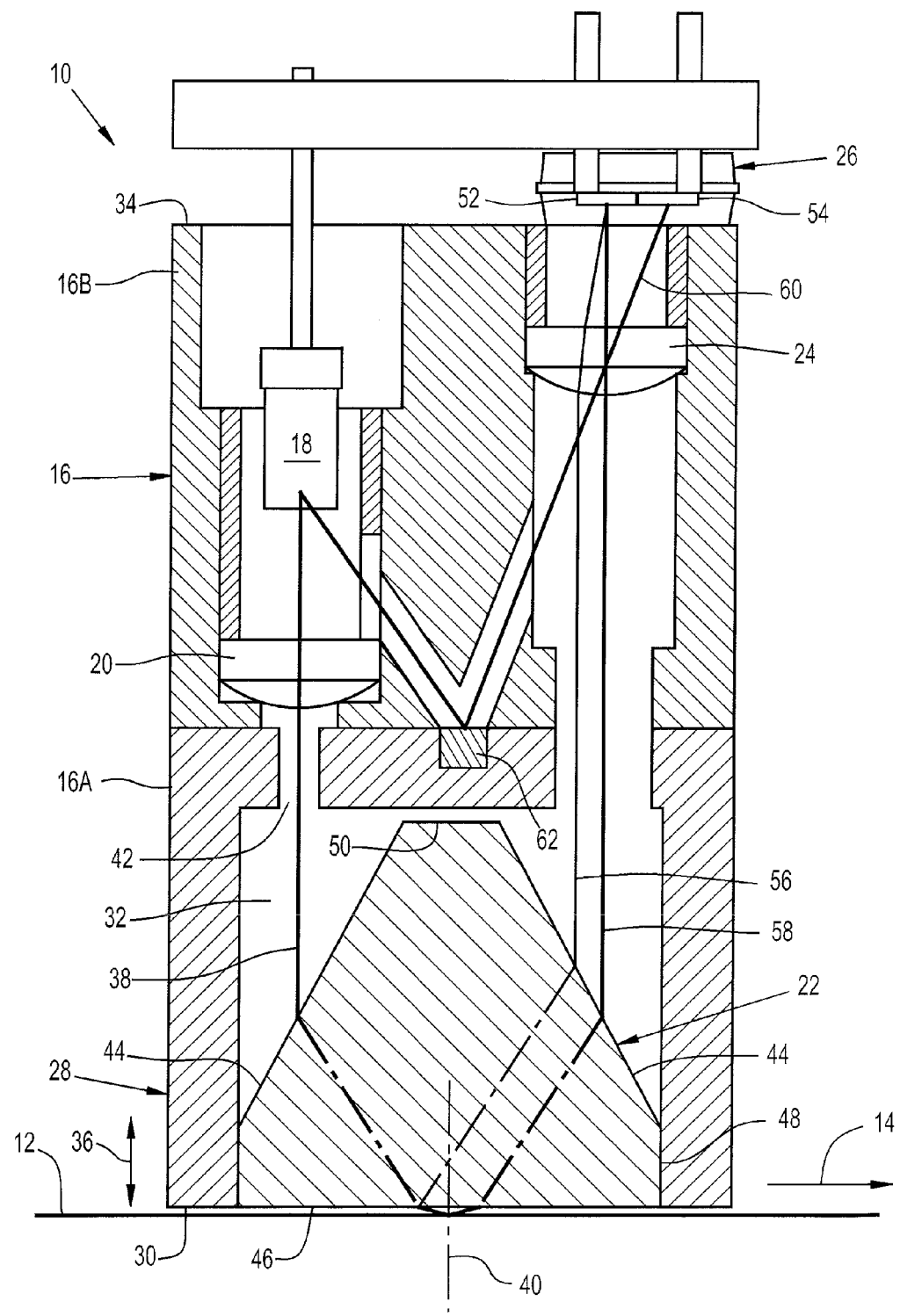
FIG. 1 is a side, sectional view of an embodiment of a gloss sensor of the present invention, in relation to a moving fiber web.
Figure 2:
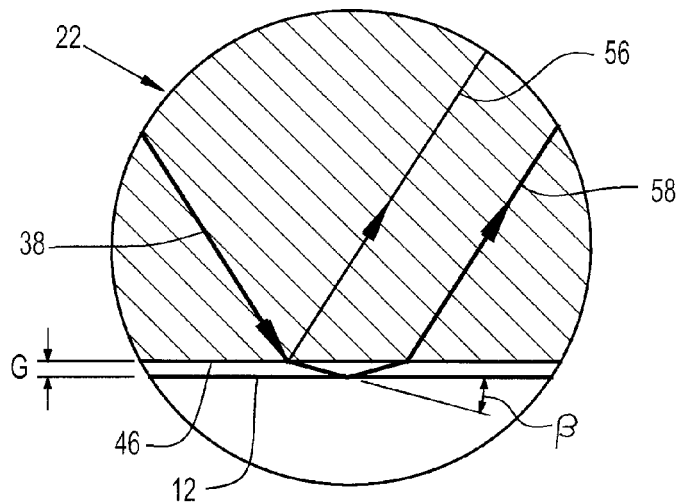
FIG. 2 is an enlarged, sectional view of a portion of the prism shown in FIG. 1 showing the internally and externally reflected light beams.
Figure 3:
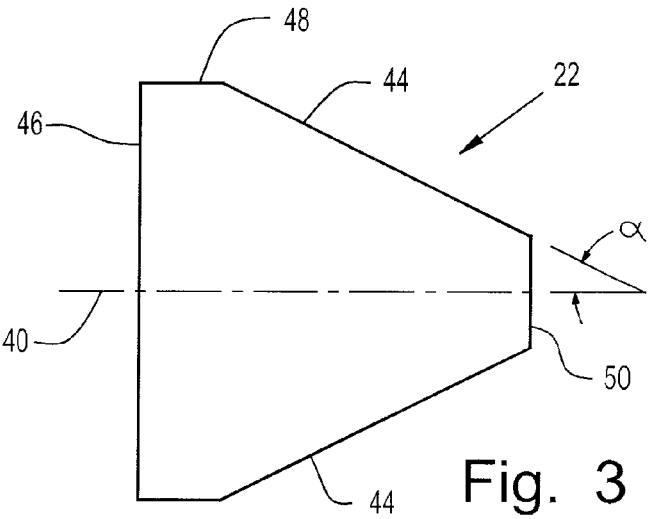
FIG. 3 is a side view of the prism shown in FIGS. 1 and 2.
Figure 4:
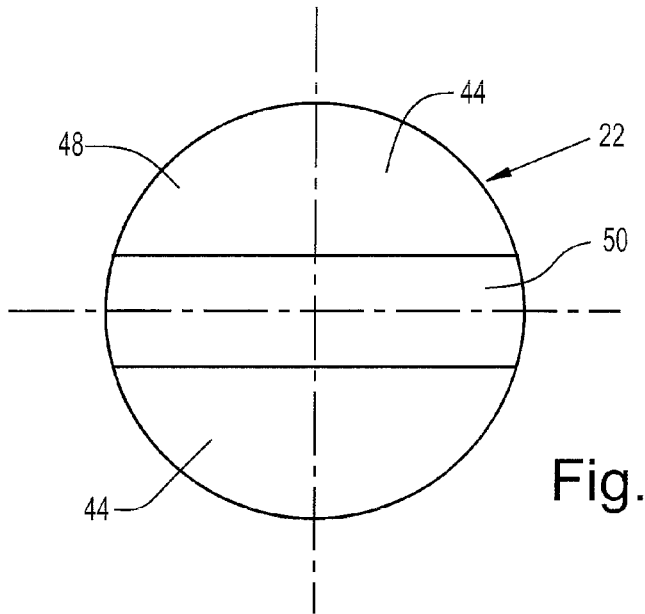
FIG. 4 is a top view of the prism shown in FIGS. 1-3.

Referring now to the drawings, and more particularly to FIGS. 1 and 2, there is shown an embodiment of a gloss sensor 10 of the present invention for optically measuring the gloss of a moving surface 12. In the embodiment shown, moving surface 12 is configured as a fiber web, such as a paper web, which moves in a machine direction 14. Gloss sensor 10 is typically moved in a cross-machine direction (i.e., transverse to machine direction 14) using suitable structure for carrying gloss sensor 10 in the cross-machine direction (not shown).

Gloss sensor 10 generally includes a housing 16, light source 18, source lens 20, optical prism 22, receiver lens 24 and a light detector assembly 26.

Housing 16 has an exterior surface 28 with an end 30 which is positioned adjacent to and generally parallel with moving surface 12. A cylindrical opening 32 is formed in end 30 for receiving prism 22, as will be described hereinafter.

In the embodiment shown, housing 16 is configured as a two piece housing with a first housing part 16A and a second housing part 16B which are joined together at a split line for manufacturing and assembly purposes. Housing part 16A includes end 30 which is adjacent to moving surface 14, and housing part 16B includes an opposite end 34 through which light source 18, source lens 20 and receiver lens 24 are installed.

Housing 16, and thus gloss sensor 10 in general, may be positioned at a predetermined fixed distance relative to moving surface 12. However, in the embodiment shown, housing 16 is preferably movable in directions toward and away from moving surface 12, as indicated by double headed arrow 36. Suitable structure for moving a gloss sensor toward and away from a moving fiber web are known in the industry, and thus not shown or described herein in more detail for purposes of simplicity.

Light source 18 is carried by housing 16 and may be of known design for emitting a source beam 38 of light in a direction generally parallel to a longitudinal axis 40 of prism 22.

Source lens 20 may be of known construction, and focuses source beam 38 through a source aperture 42. Source beam 38 passes through source aperture 42, and impinges upon prism 22, as will be described in more detail below.

Prism 22 is carried by housing part 16A adjacent to housing end 30. Prism 22 is preferably a glass prism, more preferably a solid crystal prism, and in the embodiment shown is a solid sapphire prism. Referring to FIGS. 1-4, conjunctively, prism 22 basically has a cylindrical shape, onto which a pair of opposing side facets 44 are formed. More particularly, prism 22 has a generally planar surface 46 which is mounted flush with housing end 30, thereby being continuous and not recessed relative to housing end 30. Mounting prism 22 such that planar surface 46 is flush with housing end 30 avoids buildup of dirt, residue, fibers, etc. Planar surface 46 may be finished with a surface finish common for optics.

Planar surface 46 may be coated with a coating (not specifically shown since it is very thin) which provides prism 22 with a desired internal reflectance. Moreover, as indicated above, gloss sensor 10, and thus planar surface 46, is movable toward and away from moving surface 12. In the embodiment shown, gloss sensor 10 is movable toward and away from moving surface 12 such that a gap G (FIG. 2) exists between planar surface 46 and moving surface 12. Gap G is preferably approximately 0.05 to 0.5 mm from moving surface 12; and more preferably is approximately 0.2 mm from moving surface 12.

Prism 22 also includes an annular surface 48 which is adjacent to planar surface 46 and generally concentric around longitudinal axis 40. Annular surface 48 allows prism 22 to be received in an aligned manner within cylindrical opening 32 of housing 16, and held in place by a friction fit or adhesive.

Side facets 44 are positioned generally symmetrical to each other on either side of longitudinal axis 40, and each generally lie in a plane which is substantially perpendicular to the drawing plane of FIG. 1. Side facets 44 are positioned at an angle α (FIG. 3) relative to longitudinal axis 40, allowing both source light 18 and light detector assembly 26 to be positioned at a common opposite end 34 of housing 16 for effective miniaturization of gloss sensor 10. In the embodiment shown, each side facet 44 is positioned at an angle α of between approximately 20 to 30° relative to longitudinal axis 40, and more preferably is positioned at an angle of approximately 26.5° relative to longitudinal axis 40. Side facets 44 are also polished to a surface finish which is usual for optics.

Side facets 44 could be configured to terminate along a common line apex at a side opposite planar surface 46. However, for compactness of gloss sensor 10, prism 22 is preferably truncated to define a land 50 at an end opposite from planar surface 46.

Receiver lens 24 may be of known construction, and functions to focus the various light beams (to be described in more detail hereinafter) on light detector assembly 26. Light detector assembly 26 includes a primary detector 52 and a secondary detector 54. Primary detector 52 receives a reference beam 56 and a measurement beam 58 which are transmitted through prism 22. Secondary detector 54 receives a secondary reference beam 60 which is reflected from a secondary reference reflector 62. The use of a secondary reference beam is optional, as will be described in greater detail with reference to the method of operation below, and thus secondary reference reflector 62 and secondary detector 54 may be omitted for certain applications. Secondary reference reflector 62 has known optical qualities providing a gloss standard for secondary reference beam 60 which passes through receiver lens 24 and is sensed by secondary detector 54.

In the embodiment shown and described above, a single receiver lens 24 directs reference beam 56 and measurement beam 58 to a common primary detector 52. However, it is also possible to guide reference beam 56 and measurement beam 58 to spatially separate detectors and measure them separately and simultaneously. For example, receiver lens 24 can direct measurement beam 58 to primary detector 52, and an additional receiver lens (not shown) can direct reference beam 56 to another detector (not shown) which is spatially separate from primary detector 52 or secondary detector 54.

During operation, the source beam from light source 18 is projected through source lens 20 and a rectangular source aperture 42 onto a side facet 44 of a prism 22. Part of the source beam 38 exits prism 22 and part is internally reflected from planar surface 46 of prism 22. The internal reflection from planar surface 46 of prism 22 can be used as an internal gloss standard, and the magnitude of this reference signal for reference beam 56 can be adjusted by selecting a prism material that has the desired refractive index. It also can be adjusted (reduced) by applying an anti-reflection coating on the planar surface 46. The internal signal is measured by opening the measuring gap G, in which case only the internal reference reflection is seen by primary detector 52. When primary detector 52 is measuring moving surface 12, the value of reference beam 56 is subtracted from measurement beam 58.

The part of source beam 38 that exits prism 22 is reflected back to prism 22 from moving surface 12 that is measured, and the amount of this reflection depends on the gloss of the moving surface. The beam that is reflected back from the moving surface 12 is the measurement beam 58 that will be parallel with the primary reference beam 56 and both beams pass through receiver lens 24 and reach the primary detector 52.

The optional secondary reference beam 60 is taken directly from the light source 18 via secondary reference reflector 62 through receiver lens 24 to the secondary detector 54. The purpose of secondary reference beam 60 is to monitor possible variations in the intensity of light source 18 and to provide a fast correction for these variations.

The primary reference beam 56 measures the strength of the optical signal through approximately the same path as the measurement beam 58 travels. This is done by lifting the sensor away from the sheet and by measuring the signal from primary detector 52. If the optional secondary reference beam 60 is not used, then gloss is measured using the following formula:

$$\text{Gloss} = A*[(M/P) - B]$$

Where: A and B are calibration constants. M is the signal from the primary detector 52 during normal measurement and P is the signal from the primary detector 52 with the gloss sensor 10 lifted off from the sheet.

If the secondary reference is also used, then the formula is:

$$\text{Gloss} = A*\{[(M/S)/(P/SO)] - B\}$$

Where: S is the signal from the secondary detector 54 measured at the same time as M and SO is the signal from the secondary detector 54 measured when signal P was recorded.

In some cases it may be advantageous to use anti-reflection coating on the planar surface 46 of prism 22 making the signal from the primary reference beam 56 very small. In that case the primary reference intensity may become too small to be useful. It may thus be necessary to either use the signal from the measurement beam 58 alone and just rely on the stability of the system, or use the signal for the secondary reference beam 60. If only the signal for the measurement beam 58 is used, the formula for gloss is:

$$\text{Gloss} = A*(M - B)$$

If the secondary reference beam 60 is used together with the signal for measurement beam 58, then the formula for gloss becomes:

$$\text{Gloss} = A*(M/S - B)$$

Gloss sensor 10 can also be placed periodically on a standard disk or sheet with a known gloss. The reading taken on this standard can be used to update calibration constant A:

$$\text{New } A = (\text{Old } A)*(\text{Standard/Gloss})$$

Where: Standard is the known gloss value for the standard sample and Gloss is the gloss reading for that standard sample using the old A-value.

From the foregoing, it is apparent that gloss sensor 10 provides a gloss sensor with a continuous smooth surface without sacrificing the accuracy of the measurement. Moreover, the light path through prism 22 can be bent in such a way that gloss sensor 10 can be made very small making it possible to mount it on an air bearing support. Due to the small size it can also be easily oriented to measure the gloss of a moving fiber web 12 in a machine direction.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A gloss sensor for optically measuring the gloss of a moving surface, comprising:
   a housing having an exterior surface which is generally parallel with the moving surface;
   a light source carried by said housing and configured for emitting a source beam of light;
   at least one light detector carried by said housing; and
   an optical prism mounted to said housing at said exterior surface, said prism being configured to split said source beam into a reference beam which is reflected by said prism internally within said housing to said at least one light detector, and a measurement beam which passes through said prism and is reflected by the moving surface to said at least one light detector.

2. The gloss sensor of claim 1, wherein said prism is mounted flush with said exterior surface of said housing.

3. The gloss sensor of claim 2, wherein said exterior surface and said prism are continuous and have an absence of any recess.

4. The gloss sensor of claim 3, wherein said exterior surface is at an end of said housing, and said light source and each said light detector are positioned at an opposite end of said housing.

5. The gloss sensor of claim 1, wherein said at least one light detector includes a primary detector, and further including a receiver lens interposed between said prism and said primary detector in a path of each of said reference beam and said measurement beam.

6. The gloss sensor of claim 5, wherein said at least one light detector includes a secondary detector, and further including a secondary reference reflector carried by said housing, said secondary reference reflector configured to reflect a secondary reference beam which is transmitted through said receiver lens to said secondary detector.

7. The gloss sensor of claim 1, wherein said prism comprises a glass prism.

8. The gloss sensor of claim 7, wherein said prism comprises a solid crystal prism.

9. The gloss sensor of claim 7, including a coating on said prism which provides said prism with a desired internal reflectance.

10. The gloss sensor of claim 1, wherein said prism is configured such that said measurement beam impinges upon the moving surface at an angle of between 45 to 90 degrees.

11. The gloss sensor of claim 10, wherein said prism is configured such that said measurement beam impinges upon the moving surface at an angle of approximately 75 degrees.

12. The gloss sensor of claim 1, wherein said housing is movable toward and away from the moving surface.

13. The gloss sensor of claim 1, wherein said prism is configured to be positioned at a distance of between approximately 0.05 to 0.5 mm from the moving surface.

14. The gloss sensor of claim 13, wherein said prism is configured to be positioned a distance of approximately 0.2 mm from the moving surface.

15. The gloss sensor of claim 1, wherein said gloss sensor optically measures a moving surface in the form of a fiber web in a paper machine.

16. A gloss sensor for optically measuring the gloss of a moving surface, comprising:
   a housing having an end adjacent to the moving surface and an opposite end;
   an optical prism mounted to said housing end, said prism having a longitudinal axis, a planar surface adjacent to and generally parallel with the moving surface, and a pair of opposing side facets on each side of said longitudinal axis;
   a light source carried by said housing opposite end and configured for emitting a source beam of light in a direction generally parallel to said longitudinal axis for impingement upon one of said side facets; and
   at least one light detector carried by said housing opposite end.

17. The gloss sensor of claim 16, wherein said prism is configured to split said source beam into a reference beam which is reflected by said planar surface of said prism internally within said housing to said at least one light detector, and a measurement beam which passes through said planar surface of said prism and is reflected by the moving surface to said at least one light detector.

18. The gloss sensor of claim 16, wherein each said side facet is generally symmetrically positioned at an angle of between approximately 20 to 30 degrees to said longitudinal axis.

19. The gloss sensor of claim 18, wherein each said side facet is generally concentrically positioned at an angle of approximately 26.5 degrees to said longitudinal axis.

20. The gloss sensor of claim 16, wherein said prism is truncated at an end away from said planar surface.

21. The gloss sensor of claim 16, wherein said prism has an annular surface adjacent said planar surface which is generally concentric around said longitudinal axis.

22. The gloss sensor of claim 16, further including a source lens and a source aperture between said light source and said prism, said source aperture configured to allow said source beam of light to pass therethrough and impinge upon said one prism facet.

23. The gloss sensor of claim 16, wherein said gloss sensor optically measures a moving surface in the form of a fiber web in a paper machine.

24. A method of measuring the gloss of a moving surface, comprising the steps of:
   positioning a gloss sensor housing such that an exterior surface of the housing is adjacent and generally parallel to the moving surface at a distance of between approximately 0.05 to 0.5 mm from the moving surface;
   emitting a source beam of light from a light source carried by said housing;
   splitting said source beam into a reference beam and a measurement beam using an optical prism mounted to said housing at said exterior surface, said reference beam being reflected by said prism internally within said housing to said at least one light detector, and a measurement beam which passes through said prism and is reflected by the moving surface to said at least one light detector; and
   receiving each of said reference beam and said measurement beam at least one light detector carried by said housing.

25. The method of measuring the gloss of a moving surface of claim 24, wherein said exterior surface and said prism are continuous and have an absence of any recess.

26. The method of measuring the gloss of a moving surface of claim 25, wherein said exterior surface is at an end of said housing, and said light source and each said light detector are positioned at an opposite end of said housing.

27. The method of measuring the gloss of a moving surface of claim 24, wherein said at least one light detector includes a primary detector, and further including a receiver lens interposed between said prism and said primary detector in a path of each of said reference beam and said measurement beam.

28. The method of measuring the gloss of a moving surface of claim 27, wherein said at least one light detector includes a secondary detector, and further including a secondary reference reflector carried by said housing, and including the steps of splitting said source beam into a secondary reference beam using said secondary reference reflector, and transmitting said secondary reference beam through said receiver lens to said secondary detector.

29. The method of measuring the gloss of a moving surface of claim 24, including the steps of reflecting said measurement beam from the moving surface and passing said measurement beam back through said prism before reaching said at least one detector.

* * * * *